(12) United States Patent
Borzilleri et al.

(10) Patent No.: US 7,851,489 B2
(45) Date of Patent: Dec. 14, 2010

(54) PYRIDINONE COMPOUNDS

(75) Inventors: Robert M. Borzilleri, New Hope, PA (US); Gretchen M. Schroeder, Ewing, NJ (US); Zhen-Wei Cai, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 461 days.

(21) Appl. No.: 11/936,984

(22) Filed: Nov. 8, 2007

(65) Prior Publication Data

US 2008/0114033 A1 May 15, 2008

Related U.S. Application Data

(60) Provisional application No. 60/857,540, filed on Nov. 8, 2006.

(51) Int. Cl.
C07D 401/02 (2006.01)
A61K 31/44 (2006.01)

(52) U.S. Cl. .................................. 514/332; 546/261

(58) Field of Classification Search .................. None
See application file for complete search history.

(56) References Cited

U.S. PATENT DOCUMENTS

| | | | |
|---|---|---|---|
| 6,143,764 A | 11/2000 | Kubo et al. | |
| 6,355,660 B1 | 3/2002 | Ricks et al. | |
| 6,429,213 B1 | 8/2002 | Xue et al. | |
| 6,521,622 B1 | 2/2003 | Ricks et al. | |
| 6,696,487 B2 | 2/2004 | Gerusz et al. | |
| 6,706,740 B2 | 3/2004 | Ricks et al. | |
| 6,858,626 B2 | 2/2005 | Xue et al. | |
| 7,173,031 B2 | 2/2007 | Borzilleri et al. | |
| 2003/0082631 A1 | 5/2003 | Gustavsson et al. | |
| 2005/0038035 A1 | 2/2005 | Takasugi et al. | |
| 2005/0245530 A1 | 11/2005 | Borzilleri et al. | |
| 2005/0288289 A1 | 12/2005 | Crispino et al. | |
| 2005/0288290 A1 | 12/2005 | Borzilleri et al. | |
| 2006/0009453 A1 | 1/2006 | Geuns-Meyer et al. | |
| 2006/0211695 A1 | 9/2006 | Borzilleri et al. | |
| 2007/0060613 A1 | 3/2007 | Kim | |
| 2007/0117802 A1 | 5/2007 | Borzilleri et al. | |
| 2007/0123534 A1 | 5/2007 | Cai et al. | |
| 2007/0219215 A1 | 9/2007 | Kato et al. | |

FOREIGN PATENT DOCUMENTS

| | | |
|---|---|---|
| EP | 430885 | 6/1991 |
| WO | WO 97/17329 | 5/1997 |
| WO | WO 01/21596 | 3/2001 |
| WO | WO 2005/026124 | 3/2005 |
| WO | WO 2006/116713 | 11/2006 |

OTHER PUBLICATIONS

PCT international Search Report and Written Opinion (Feb. 26, 2008).

*Primary Examiner*—Zinna N Davis
(74) *Attorney, Agent, or Firm*—Gary D. Greenblatt; Maureen S. Gibbons

(57) ABSTRACT

The invention is directed to pyridinone compounds useful for modulating Met kinase, having the following structure:

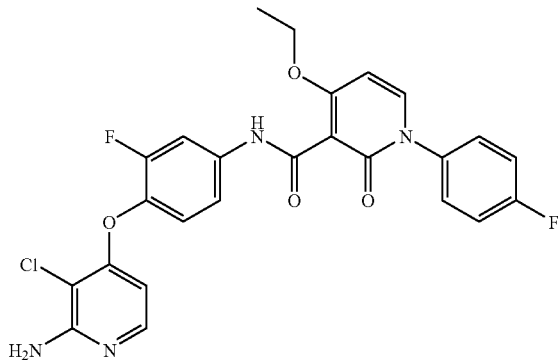

and is further directed to pharmaceutical compositions comprising the compound; and methods for treating proliferative diseases, such as cancer by the administration of this compound.

5 Claims, 2 Drawing Sheets

PYRIDINONE COMPOUNDS

This application claims benefit of 60/857,540 filed Nov. 8, 2006.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54, 1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65, 1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer*, 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS*, 94:701-6, 1997) and an amplified/overexpressed Met spontaneously transforms NIH-3T3 cells (Cooper et al., *EMBO J.*, 5:2623-8, 1986).

Biological agents, such as ribozymes, antibodies and antisense RNA targeting either HGF or Met have been shown to inhibit tumorogenesis (Stabile et al., *Gene Therapy*, 11:325-35, 2004, Jiang et al., *Clin. Cancer Res*, 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

There are several patent applications directed to compounds that are useful for treating Met activated cancers. For example, see U.S. Published Patent US2005/0245530, published Nov. 3, 2005, the disclosure of which is herein incorporated by reference. However, Applicants have found that the compounds of the present invention are surprisingly advantageous.

SUMMARY OF THE INVENTION

The present invention is directed to the following compound,

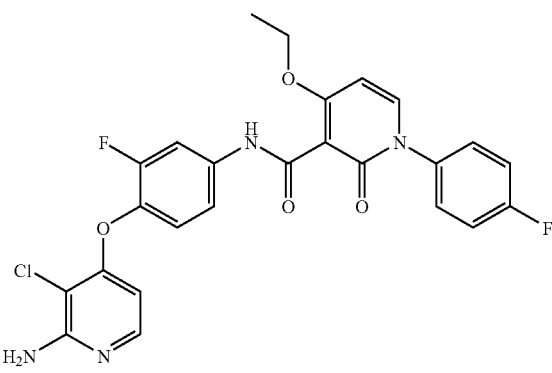

including salts thereof. Applicants have found that N-(4-(2-Amino-3-chloropyridin-4-yloxy)-3-fluorophenyl)-4-ethoxy-1-(4-fluorophenyl)-2-oxo-1,2-dihydropyridine-3-carboxamide (Compound 1) and salts thereof, are especially useful for treating Met-related cancers due to its combination of increased potency and reduced inhibition against certain CYP 450 isozymes compared to some known Met kinase inhibitors.

The present invention is also directed to pharmaceutical compositions comprising a therapeutically effective amount of Compound 1, as described above, or a salt thereof in a pharmaceutically acceptable carrier.

The present invention is further directed to methods of treating cancer in a patient in need of such treatment wherein the cancer is dependent upon Met activation, wherein the Met activation is regulated by gene amplification, an activated Met mutation and/or HGF stimulation, comprising administering to the patient a therapeutically effective amount of Compound 1 and alternatively administering at least one additional anticancer agent.

In some embodiments of the present invention, the cancer to be treated is selected from bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma.

DETAILED DESCRIPTION

Figure 1:
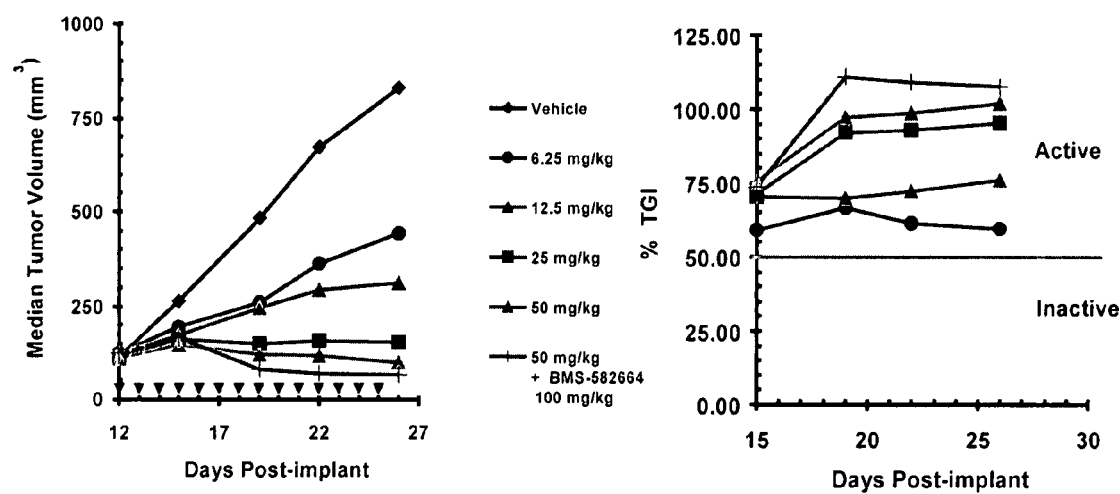
FIG. 1 shows antitumor activity against GTL-16 gastric carcinoma xenografts.

Listed below are definitions of various terms used to describe the present invention. These definitions apply to the terms as they are used throughout the specification (unless they are otherwise limited in specific instances) either individually or as part of a larger group.

The phrase "therapeutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

The phrase "pharmaceutically acceptable salt(s)", or "salt(s)" as used herein, unless otherwise indicated, includes salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, sulfate, benzenesulfonate, p-toluenesulfonate and pamoate [i.e., 1,1'-methylene-bis-(2-hydroxy-3-naphthoate)] salts.

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of HGF to bind its cognate receptor (Met) in such a way as to activate the receptor that results in a phenotypic response. In the case of Met, this can be cellular proliferation, motility, differentiation and/or survival.

The term "patient" as used herein encompasses all mammalian species, including humans, cows, horses, dogs, and cats.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The present invention is directed to the following Compound 1:

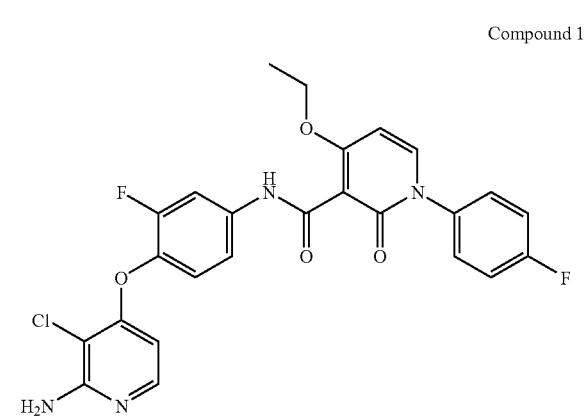

Compound 1 or salts thereof, which are useful for the treatment of cancer. It has been found that the compounds of the present invention are especially useful for treating cancer because of increased potency and reduced inhibition against certain CYP 450 isozymes over known Met kinase inhibitors.

Accordingly, the present invention is directed to methods for treating cancer in a patient wherein the cancer is dependent upon Met activation, wherein the Met activation is regulated by gene amplification, an activated Met mutation and/or HGF stimulation, comprising administering to the patient a therapeutically effective amount of Compound 1, or a salt thereof.

According to one embodiment of the present invention, methods are provided for treating bladder cancer, breast cancer, colorectal cancer, gastric cancer, head and neck cancer, kidney cancer, liver cancer, lung cancer, ovarian cancer, pancreas/gall bladder cancer, prostate cancer, thyroid cancer, osteosarcoma, rhabdomyosarcoma, MFH/fibrosarcoma, glioblastomas/astrocytomas, melanoma, and mesothelioma, all of which are known to be related to Met activation.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, the compounds of the present invention may be administered in combination with other anti-cancer treatments useful in the treatment of cancer or other proliferative diseases. The invention herein further comprises use of Compound 1 or salts thereof in preparing medicaments for the treatment of cancer, and/or it comprises the packaging of Compound 1 herein together with instructions that the compound be used in combination with other anti-cancer or cytotoxic agents and treatments for the treatment of cancer. The present invention further comprises combinations of Compound 1 and one or more additional agents in kit form, e.g., where they are packaged together or placed in separate packages to be sold together as a kit, or where they are packaged to be formulated together.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof.

Separation of diastereoisomers may be achieved by conventional techniques, e.g. by fractional crystallization, chromatography or H.P.L.C. of a stereoisomeric mixture of a compound of the present invention, or a suitable salt or derivative thereof. An individual enantiomer of the compound may also be prepared from a corresponding optically pure intermediate or by resolution, such as by H.P.L.C. of the corresponding racemate using a suitable chiral support or by fractional crystallization of the diastereoisomeric salts formed by reaction of the corresponding racemate with a suitable optically active acid or base, as appropriate.

Also embraced within this invention is a class of pharmaceutical compositions comprising Compound 1 or a salt thereof in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crosspovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units were tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which were administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients were dissolved or suspended in suitable carrier, especially an aqueous solvent for the active ingredients. The active ingredients were preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise Compound 1, or a pharmaceutically acceptable salt thereof, and optionally an additional agent selected from a kinase inhibitory agent (small molecule, polypeptide, antibody, etc.), an immunosuppressant, an anticancer agent, an antiviral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof, and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as D-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as .alpha.-, .beta.-, and .gamma.-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

EXAMPLES

The following examples and preparations describe the manner and process of making and using the invention.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using 10% methanol, 90% water, 0.1% TFA (solvent A) and 90% methanol, 10% water, 0.1% TFA (solvent B) and detection at 220 nm on one of the following columns: A—Shimadzu S50DS-VP 20×100 mm column with a flow rate of 20 mL/min; B—YMC S5 ODS 30×100 mm column with a flow rate of 20 mL/min; C—Phenomonex 30×250 mm column with a flow rate of 10 mL/min; D—YMC S5 ODS 20×250 mm column with a flow rate of 10 mL/min; E—YMC S10 ODS 50×500 mm column with a flow rate of 50 mL/min; or F—YMC S11 ODS 30×500 mm column with a flow rate of 20 mL/min.

The final product was characterized by $^1$H NMR, RP HPLC, electrospray ionization (ESI MS) or atmospheric pressure ionization (API MS) mass spectrometry. $^1$H NMR spectra were obtained on a 400 MHz Bruker instrument. $^{13}$C NMR spectra were recorded at 100 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; TEA: triethylamine; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT or rt: room temperature; tR: retention time; h: hour(s); min: minute(s); PyBroP: bromotripyrrolidinophosphonium hexafluorophosphate; TBTU: O-(1H-benzotriazol-1-yl)-N,N,N'N'-tetramethyluronium tetrafluoroborate; DMAP: 4-N,N-dimethylaminopyridine; HOBt or HOBT: hydroxybenzotriazole; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; Et$_2$O: diethyl ether; DCM: dichloromethane or methylene chloride; m-CPBA: 4-chloroperoxybenzoic acid.

Example 1

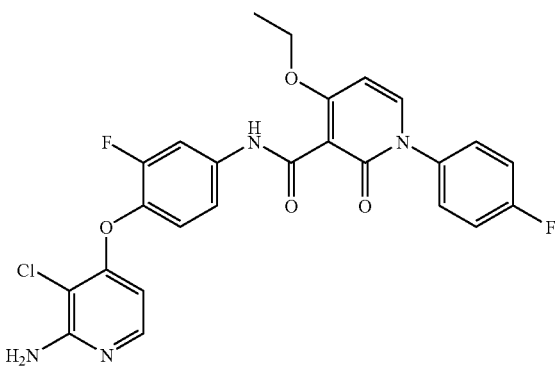

N-(4-(2-Amino-3-chloropyridin-4-yloxy)-3-fluorophenyl)-4-ethoxy-1-(4-fluorophenyl)-2-oxo-1,2-dihydropyridine-3-carboxamide

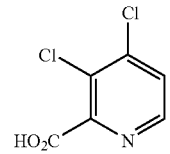

A) 3,4-Dichloropicolinic acid

As described previously by Marzi, E. et al. (*Eur. J. Org. Chem.* 2001, 1371-1376), 2,2,6,6-tetramethylpiperidine (8.84 mL, 52 mmol, Aldrich) in 50 mL of ether at 0° C. was charged with n-BuLi (33 mL, 52 mmol, Aldrich, 1.6 M hexanes). After stirring at 0° C. for 30 min, the solution was cooled to −78° C. and charged with a solution of 3,4-dichloropyridine (7.0 g, 47 mmol, Matrix) in 5 mL of ether. After stirring at −78° C. for 2 h, carbon dioxide (dry ice) was bubbled into the reaction mixture via cannula at which time the solution became heterogeneous. After bubbling carbon dioxide into the reaction at −78° C. for 10 min, the cooling bath was removed and the reaction mixture was allowed to warm to rt with $CO_2$ bubbling. The reaction was quenched with saturated aqueous ammonium chloride solution (~50 mL) and stirred at rt under an atmosphere of air for 5 min. The reaction mixture was diluted with water (~150 mL) and extracted with ethyl acetate (2×75 mL) to remove any remaining starting material. The aqueous layer was acidified to pH 1-2 with 1N aqueous HCl solution and extracted with ethyl acetate (2×100 mL). The organic phase was dried over anhydrous magnesium sulfate and concentrated in vacuo to give 3,4-dichloropicolinic acid (3.5 g, 39%) as a yellow solid. $^1$H NMR (DMSO-$d_6$) δ 8.53 (d, 1H, J=5.2 Hz), 7.90 (d, 1H, J=5.2 Hz); MS (ESI$^+$) m/z 192.08 (M+H)$^+$.

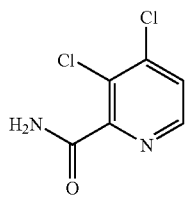

B) 3,4-Dichloropicolinamide

A mixture of 3,4-dichloropicolinic acid (3.5 g, 18 mmol) in excess thionyl chloride (10 mL, Aldrich ReagentPlus 99.5%) was stirred at 80° C. for 1 h. After cooling to rt, the reaction was concentrated in vacuo to remove excess thionyl chloride and then suspended in ether (50 mL). The ethereal acid chloride solution was added to ammonium hydroxide (50 mL) at 0° C. The product was collected by vacuum filtration, washed with water, and then triturated with ether to give 3,4-dichloropicolinamide (2.6 g, 76%) as a beige solid. $^1$H NMR (DMSO-$d_6$) δ 8.50 (d, 1H, J=5.2 Hz), 8.12 (br s, 1H), 7.83 (d, 1H, J=5.2 Hz), 7.82 (br s, 1H); MS (ESI$^+$) m/z 191.10 (M+H)$^+$.

Alternatively, 3,4-dichloropicolinamide can be prepared directly from 3,4-dichloropyridine according to the procedure described below.

To a solution of 2,2,6,6-tetramethylpiperidine (31.1 g, 0.22 mol) in diethyl ether (400 mL) at 0° C. was added n-BuLi in hexane (1.6 M, 138.0 mL, 0.22 mol) via syringe over 15 min. The resulting solution was stirred at 0° C. for 0.5 h and at −78° C. for 0.5 h. To this mixture was then slowly added a solution of 3,4-dichloropyridine (29.6 g, 0.20 mol) in diethyl ether (20 mL) via syringe over 15 min. The resulting mixture was stirred at −78° C. for 2 h before the addition of isocyanatotrimethylsilane (85% pure, 40.0 mL, 0.30 mol). The source for isocyanatotrimethylsilane is TCI. After the addition, the cooling bath was removed and the reaction mixture was allowed to warm to room temperature over 1 h. The reaction mixture was quenched with acetic acid (40 g, 0.67 mol) and 200 mL of water. The mixture was allowed to stir overnight and the white solid that formed was collected through filtration and washed with water. The filtrate was extracted with ethyl acetate (3×300 mL). The solid that was collected previously was dissolved in the combined organic layers, and the resulting solution was washed with brine (2×200 mL), dried over $MgSO_4$ and concentrated in vacuo. The residue was suspended in 200 mL of diethyl ether and sonicated. The remaining solid was collected through filtration and washed with minimum amount of diethyl ether to provide 3,4-dichloropicolinamide (14.8 g, 39%).

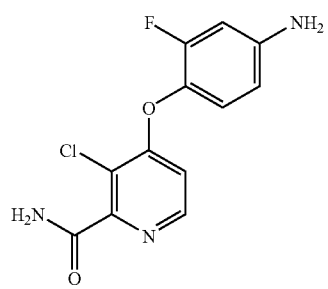

C) 4-(4-Amino-2-fluorophenoxy)-3-chloropicolinamide

To a solution of 4-amino-2-fluorophenol (9.3 g, 73 mmol, 3B Medical Systems, 3B3290) in DMF (100 mL) was added potassium tert-butoxide (8.8 g, 79 mmol). After stirring at rt for 30 min, 3,4-dichloropicolinamide (10 g, 52 mmol) was added. The reaction mixture was stirred at 50° C. for 2.5 h. After cooling the reaction to rt, the mixture was diluted with 400 mL of ethyl acetate and washed with saturated aqueous sodium bicarbonate solution (400 mL). The aqueous layer was back-extracted with 300 mL ethyl acetate. The combined organic phases were washed with 10% aqueous lithium chloride solution, dried over anhydrous sodium sulfate, and concentrated in vacuo. The resulting brown solid was suspended in ethyl acetate, filtered and washed with ether to give the product as a tan solid (7.4 g). The filtrate was concentrated in vacuo and then purified by flash chromatography on silica gel (2% methanol/ethyl acetate). The resulting brown solid was triturated with ether to give an additional 4.3 g of 4-(4-amino-2-fluorophenoxy)-3-chloropicolinamide (79% combined yield) as a pale tan solid. $^1$H NMR (CD$_3$OD) δ 8.29 (d, 1H, J=5.6 Hz), 7.00 (t, 1H, J=8.8 Hz), 6.79 (d, 1H, J=5.6 Hz), 6.63-6.55 (m, 2H); MS (ESI$^+$) m/z 282.21 (M+H)$^+$.

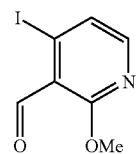

D) 4-Iodo-2-methoxynicotinaldehyde

To a solution of diisopropylamine (260 g, 2.57 mol) in anhydrous THF (6.5 L) at −30 to −40° C. under a blanket of $N_2$ was added n-BuLi (156 g, 2.45 mol) dropwise via cannula. The resulting solution was allowed to warm to 0° C. and stirred at this temperature for 35 min. The solution was then cooled to −78° C. and 2-fluoropyridine (250 g, 2.57 mol, Alfa)

was added dropwise. The reaction mixture was stirred at −78° C. for 2 h. This mixture was then added via cannula to a solution of iodine (654 g, 2.57 mol) in anhydrous THF (1.96 L) at −20° C. under $N_2$. After the reaction was complete, the mixture was quenched with ice water and extracted with EtOAc. The organic layer was washed with sodium thiosulfate followed by water and brine. The organics were then dried ($Na_2SO_4$) and concentrated in vacuo to give 2-fluoro-3-iodopyridine (450 g, 78%) as a solid, which was sufficiently pure to use in the subsequent step.

To a solution of diisopropylamine (345 mL, 249 g, 2.46 mol) in anhydrous THF (5 L) at −8 to −10° C. under a blanket of $N_2$ was added n-BuLi (880 mL, 158 g, 2.46 mol) dropwise via cannula. The mixture was stirred at −10° C. for 30 min, cooled to −78° C. and treated with a solution of 2-fluoro-3-iodopyridine (500 g, 2.24 mol) in dry THF (2 L) dropwise. After the addition, the reaction mixture was warmed to −60° C. and this temperature was maintained for 2 h. The mixture was then cooled to −78° C., treated with ethyl formate (183 g, 2.47 mol) dropwise, followed by sodium methoxide (149 g, 2.75 mol) in MeOH (1.5 L) and warmed to ambient temperature. The reaction mixture was quenched with ice water and extracted with EtOAc. The layers were separated and the organic phase was washed with water and brine, dried ($Na_2SO_4$) and concentrated in vacuo. The residue was purified by flash chromatography on silica gel to afford 4-iodo-2-methoxynicotinaldehyde (380 g, 64%) as a solid.

Alternatively, 4-iodo-2-methoxynicotinaldehyde can be prepared according to the procedure described in U.S. Pat. No. 5,491,237 (WO 95/29917).

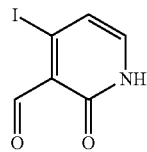

E)
4-Iodo-2-oxo-1,2-dihydropyridine-3-carbaldehyde

4-Iodo-2-methoxynicotinaldehyde (25 g, 95 mmol) and sodium iodide (31.0 g, 285 mmol, Aldrich) were stirred together in 500 mL of acetonitrile. To this solution was added chlorotrimethylsilane (36.0 mL, 285 mmol, Aldrich ≧99%) dropwise over 15 minutes. The reaction mixture was stirred for 2 h at room temperature and then concentrated under vacuum. The product was suspended in ethyl acetate, water, and saturated aqueous sodium bicarbonate, then filtered to give a dark brown solid. This solid was triturated with acetonitrile to yield 4-iodo-2-oxo-1,2-dihydropyridine-3-carbaldehyde (21.3 g, 90%) as a yellow solid (mixture of tautomers). MS (ESI$^+$) m/z 250.04 (M+H)$^+$.

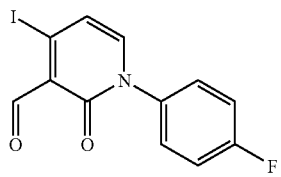

F) 1-(4-Fluorophenyl)-4-iodo-2-oxo-1,2-dihydropyridine-3-carbaldehyde

4-Iodo-2-oxo-1,2-dihydropyridine-3-carbaldehyde (16.0 g, 64.3 mmol), 4-fluorophenylboronic acid (26.8 g, 193 mmol, Aldrich), copper(II) acetate (23.4 g, 129 mmol, Aldrich), and myristic acid (58.7 g, 257 mmol, Aldrich) were stirred together in 800 mL of toluene. To this solution was added 2,6-lutidine (60 mL, 514 mmol, Aldrich) and the reaction was stirred vigorously for 1 day. An additional 5 g of 4-fluorophenylboronic acid was added and the reaction was stirred vigorously for an additional 3 days. The reaction mixture was concentrated and then suspended in 10% methanol/ethyl acetate. Celite® was added and the mixture was stirred for 5 minutes. Next the mixture was filtered through a plug of Celite®, concentrated, and suspended in ethyl acetate and water. The mixture was filtered through Celite® again to remove additional copper that had precipitated out, washing well with ethyl acetate. The filtrate was washed with 1N aqueous HCl, dried over sodium sulfate, filtered, and concentrated under vacuum. The resulting solid was triturated with ethyl acetate to yield 9.25 g (42%) of 1-(4-fluorophenyl)-4-iodo-2-oxo-1,2-dihydropyridine-3-carbaldehyde as a yellow solid. The filtrate was concentrated in vacuo and the remaining solid was triturated again with ethyl acetate to yield an additional 5.75 g (68% total yield) of the desired product as a yellow solid. $^1$H NMR (DMSO-$d_6$) δ 9.57 (s, 1H), 7.68 (d, 1H, J=7.2 Hz), 7.58-7.54 (m, 2H), 7.40 (t, 2H, J=8.8 Hz), 7.02 (d, 1H, J=7.2 Hz); MS (ESI$^+$) m/z 344.13 (M+H)$^+$.

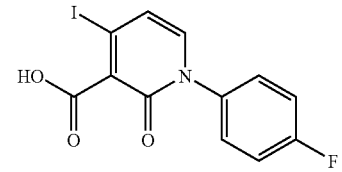

G) 1-(4-Fluorophenyl)-4-iodo-2-oxo-1,2-dihydropyridine-3-carboxylic acid 1-(4-Fluorophenyl)-4-iodo-2-oxo-1,2-dihydropyridine-3-carbaldehyde (10.0 g, 29.2 mmol) and sodium phosphate monobasic (10.1 g, 73 mmol, Aldrich) were stirred vigourously in 35 mL each of THF, tert-butanol, and water at 0° C. 2-Methyl-2-butene (45.2 mL, 2.0 M in THF, Aldrich) was added to the reaction mixture, followed by sodium chlorite (6.06 g, 67.1 mmol, Aldrich). The ice bath was removed and the reaction mixture was warmed to room temperature, stirring very rapidly. After a few minutes the desired product began precipitating out of solution. Stirring was continued for 1 h, then 20 mL of 1N aqueous HCl was added, and stirring was continued for another 5 minutes. The desired product was filtered off, then washed with water, ethyl acetate, and ether. The filtrate was taken and the layers were separated. The aqueous layer was extracted with ethyl acetate. The combined organic layers were dried over magnesium sulfate, filtered, and concentrated in vacuo. The resulting solid was suspended in ethyl acetate, filtered, and washed with ethyl acetate and ether to yield additional desired product. The pale yellow solids were combined to yield 8.22 g (78%) of 1-(4-fluorophenyl)-4-iodo-2-oxo-1,2-dihydropyridine-3-carboxylic acid (92% pure, 8% starting material remaining). This material was dissolved in a minimal amount of 1N aqueous NaOH. Ethyl acetate was added and the mixture was stirred vigourously for 5 minutes. The layers were separated, and the aqueous layer was extracted with ethyl acetate. The aqueous layer was acidified, with stirring, using concentrated HCl to pH 1. The pale yellow solid that precipitated out of solution was collected, washed with water, ethyl acetate, diethyl ether and then dried under vacuum to afford 7.33 g (70%) of 1-(4-fluorophenyl)-4-iodo-2-oxo-1,2-dihydropyridine-3-carboxylic acid (95.4% pure by HPLC). $^1$H NMR (DMSO-d$_6$) δ 13.53 (s, 1H), 7.52-7.49 (m, 3H), 7.38 (t, 2H, J=8.8 Hz), 6.81 (d, 1H, J=7.2 Hz); MS (ESI$^+$) m/z 360.14 (M+H)$^+$.

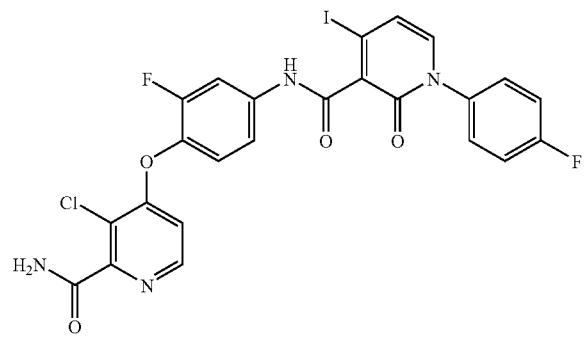

H) 3-Chloro-4-(2-fluoro-4-(1-(4-fluorophenyl)-4-iodo-2-oxo-1,2-dihydropyridine-3-carboxamido)phenoxy)picolinamide To 1-(4-fluorophenyl)-4-iodo-2-oxo-1,2-dihydropyridine-3-carboxylic acid (3.7 g, 10 mmol) in 6 mL of toluene was added thionyl chloride (10 mL, Aldrich ReagentPlus 99.5%). After stirring at rt for 2.5 h, the mixture became homogenous and was then concentrated in vacuo. Toluene (3 mL) was added to the residue and the mixture was concentrated in vacuo to remove excess thionyl chloride (performed twice). The crude acid chloride was then dried under high vacuum for 15 minutes. While the acid chloride was drying, 4-(4-amino-2-fluorophenoxy)-3-chloropicolinamide (2.5 g, 8.9 mmol) was dissolved in THF (50 mL) and DMF (3 mL). The solution was cooled to 0° C. and then N,N-diisopropylethylamine (3.1 mL, 18 mmol, Aldrich 99.5% redistilled) was added. The acid chloride was then added over 30 min as a solid. Upon completion of the addition, the cooling bath was removed and the reaction mixture was stirred at rt for 15 min before being quenched with saturated aqueous sodium bicarbonate solution (30 mL). Water was added (~30 mL) to dissolve the salts and the mixture was extracted with ethyl acetate (1×100 mL). The organic phase was dried over anhydrous sodium sulfate and concentrated in vacuo. The crude product was purified by flash chromatography on silica gel (2% methanol/ethyl acetate) to give 4.9 g of the desired product along with a minor amount of 3-chloro-4-(4-(4-chloro-1-(4-fluorophenyl)-2-oxo-1,2-dihydropyridine-3-carboxamido)-2-fluorophenoxy)picolinamide together as an off-white solid (89% based on iodide). $^1$H NMR (CD$_3$OD) δ 8.34 (d, 1H, J=5.6 Hz), 7.92 (dd, 1H, J=12.4, 2.4 Hz), 7.51-7.47 (m, 4H), 7.37-7.29 (m, 3H), 6.99 (d, 1H, J=7.2 Hz), 6.86 (d, 1H, J=5.6 Hz); MS (ESI$^+$) m/z 623.08 (M+H)$^+$.

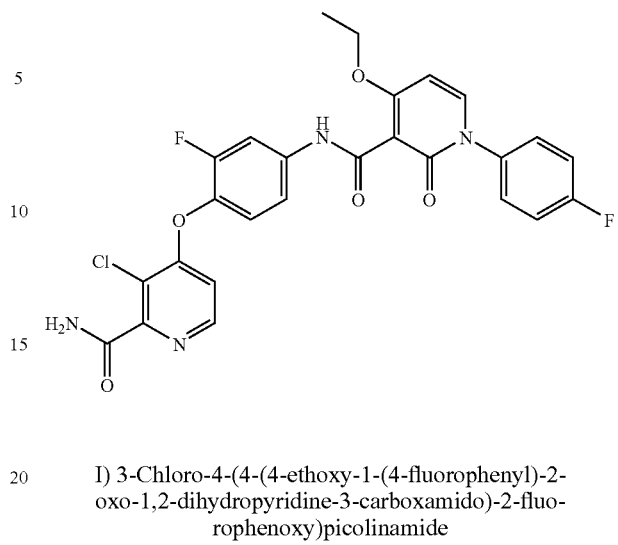

I) 3-Chloro-4-(4-(4-ethoxy-1-(4-fluorophenyl)-2-oxo-1,2-dihydropyridine-3-carboxamido)-2-fluorophenoxy)picolinamide Sodium hydride (1.89 g, 47.2 mmol, 60% dispersion in mineral oil, Aldrich) was added slowly to a solution of ethanol (77 mL, Aldrich >99.5% 200 proof) and THF (77 mL) under N$_2$ and the resulting mixture was stirred at rt for 5 min. The sodium ethoxide solution was then added to a mixture of 3-chloro-4-(2-fluoro-4-(1-(4-fluorophenyl)-4-iodo-2-oxo-1,2-dihydropyridine-3-carboxamido)phenoxy)-picolinamide and 3-chloro-4-(4-(4-chloro-1-(4-fluorophenyl)-2-oxo-1,2-dihydropyridine-3-carboxamido)-2-fluorophenoxy)picolinamide (22.6 g, ~36.3 mmol) and stirred for 1 h at rt. The reaction mixture was concentrated in vacuo. The resulting crude solid was suspended in ethyl acetate, saturated aqueous sodium bicarbonate solution, and water (to dissolve any precipitated salts). This mixture was sonicated and stirred until the remaining solid became a filterable powder. This powder was filtered off to yield 17.2 g (88%) of the desired product as a pale yellow solid. The layers of the remaining filtrate were separated. The aqueous layer was extracted with ethyl acetate. The combined organic layers were dried over anhydrous sodium sulfate and concentrated in vacuo. The resulting solid was triturated with ethyl acetate, sonicated, and filtered to give an additional 3.02 g of the desired product as a pale brown solid. $^1$H NMR (CD$_3$OD) δ 8.34 (d, 1H, J=5.6 Hz), 7.94 (dd, 1H, J=12.4, 2.4 Hz), 7.80 (d, 1H, J=8 Hz), 7.48-7.46 (m, 3H), 7.31-7.28 (m, 3H), 6.86 (d, 1H, J=5.6 Hz), 6.61 (d, 1H, J=7.2 Hz), 4.34 (q, 2H, J=7.2 Hz), 1.45 (t, 3H, J=7.2 Hz); MS (ESI$^+$) m/z 541.11 (M+H)$^+$.

J) N-(4-(2-Amino-3-chloropyridin-4-yloxy)-3-fluorophenyl)-4-ethoxy-1-(4-fluorophenyl)-2-oxo-1,2-dihydropyridine-3-carboxamide To 3-chloro-4-(4-(4-ethoxy-1-(4-fluorophenyl)-2-oxo-1,2-dihydropyridine-3-carboxamido)-2-fluorophenoxy)picolinamide (1.2 g, 2.1 mmol) in ethyl acetate (16 mL), acetonitrile (16 mL), and water (8 mL) at 0° C. was added iodobenzene diacetate (820 mg, 2.6 mmol, Aldrich). After stirring at rt for 2 h, the reaction was filtered to collect the crude product. The solid was washed with additional ethyl acetate. The filtrate was washed with saturated aqueous sodium bicarbonate solution and the organic phase was dried over anhydrous sodium sulfate and concentrated in vacuo. The precipitate and filtrate were combined and purified by flash chromatography on silica gel (2% methanol/chloroform) to give the title compound (810 mg, 74%) as a white solid. $^1$H NMR (DMSO-d$_6$) δ 10.57 (s, 1H), 7.83-7.79 (m, 2H), 7.67 (d, 1H, J=5.6 Hz), 7.41-7.38 (m, 3H), 7.36-7.22 (m, 3H), 6.44 (d, 1H, J=7.6 Hz), 6.36 (br s, 2H), 5.86 (d, 1H, J=6.0 Hz), 4.18 (q, 2H, J=7.2 Hz), 1.23 (t, 3H, J=7.2 Hz); MS (ESI$^+$) m/z 513.09 (M+H)$^+$.

Assays

The pharmacological properties of the compound of this invention may be confirmed by a number of pharmacological assays. The exemplified pharmacological assays which follow have been carried out with the compound according to the invention and/or salts thereof.

Met Kinase Assay

Incubation mixtures employed for the Met kinase assay contain a baculovirus expressed GST-Met kinase, the synthetic substrate polyGlu:Tyr, (4:1), ATP, ATP-γ-$^{33}$ P and buffer containing Mn$^{++}$, DTT, BSA, and Tris. Reactions were incubated for 60 minutes at 30° C. and stopped by the addition of cold trichloroacetic acid (TCA) to a final concentration 8%. TCA precipitates were collected onto GF/C unifilter plates (Packard Instrument Co., Meriden, Conn.) using a Filtermate universal harvester (Packard Instrument Co., Meriden, Conn.) and the filters are quantitated using a Top-Count 96/384-well liquid scintillation counter (Packard Instrument Co., Meriden, Conn.). Dose response curves were generated to determine the concentration required to inhibit 50% of kinase activity (IC__50). Compounds were dissolved at 10 mM in dimethyl sulfoxide (DMSO) and evaluated at ten concentrations, each in duplicate. The final concentration of DMSO in the assay is 1.7%. IC__50 values were derived by non-linear regression.

| Reagents | Substrate Mix Final Concentration |
|---|---|
| Stock Solution | |
| Tris-HCl, (1M, pH 7.4) | 20 mM |
| MnCl$_2$ (1M) | 1 mM |
| DTT (1M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |

| Buffer | Enzyme mix |
|---|---|
| 20 ul 1M DTT | 4 ul GST/Met enzyme(3.2 mg/ml) = 10 ng/rxn |
| 200 ul 1M Tris-HCL, pH 7.4 | qs 12 ml Buffer |
| 20 ul 100 mg/ml BSA | |
| qs 20 ml H$_2$0 | |

N-(4-(2-Amino-3-chloropyridin-4-yloxy)-3-fluorophenyl)-4-ethoxy-1-(4-fluorophenyl)-2-oxo-1,2-dihydropyridine-3-carboxamide (Compound 1) inhibits Met kinase with an IC$_{50}$ value of 3.5 nM.

In Vivo Efficacy Determination

N-(4-(2-Amino-3-chloropyridin-4-yloxy)-3-fluorophenyl)-4-ethoxy-1-(4-fluorophenyl)-2-oxo-1,2-dihydropyridine-3-carboxamide (Compound 1) was evaluated for in vivo efficacy against the GTL-16 gastric and U87 glioblastoma tumor xenografts. As illustrated in FIG. 1, Compound 1 was active as defined by greater than 50% tumor growth inhibition (TGI) for at least one tumor doubling time against the GTL-16 human gastric carcinoma model at multiple dose levels ranging from 6.25 mg/kg to 50 mg/kg. No overt toxicity was observed at all these dose levels when dosed once a day for a duration of 14 days. In this study, 25 mg/kg and 50 mg/kg resulted in complete tumor stasis. In a previously described study in which 100 mg/kg was used against this model, no increase in activity was observed. Therefore, 25 mg/kg is the observed maximum efficacious dose level for Compound 1 against the GTL-16 tumor xenograft. In this study the lowest dose level tested at 6.25 mg/kg also resulted in greater than 50% TGI and therefore, defines the minimum efficacious dose (MED) level in this study. Compound 1 was also tested against the U87 human glioblastoma model, a Met driven tumor based on an HGF autocrine mechanism of Met activation. As demonstrated in FIG. 2, complete tumor stasis was observed at both 50 and 25 mg/kg, similar to the activity observed against GTL-16 tumor xenografts.

FIG. 1. Antitumor activity against GTL-16 gastric carcinoma xenografts

Figure 2:
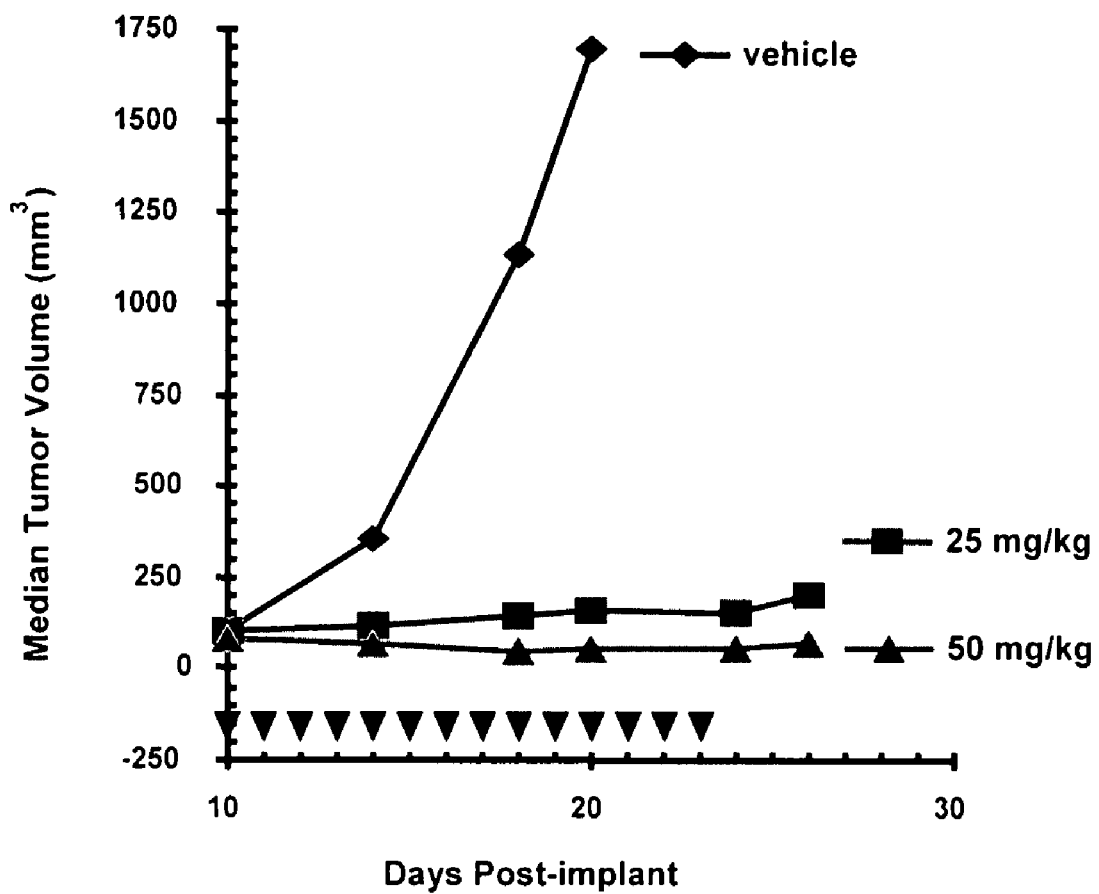
FIG. 2 shows antitumor activity against U87 glioblastoma xenografts.

FIG. 2. Antitumor activity against U87 glioblastoma xenografts

The compound of the present invention (Compound 1) has been compared to other compounds that have been found to be useful Met kinase inhibitors, such as those disclosed in US 2005/0245530, and found to be especially advantageous. For example, the compound of the present invention has been found to be especially advantageous over N-(4-(2-Aminopyridin-4-yloxy)-3-fluorophenyl)-1-(4-fluorophenyl)-2-oxo-1,2-dihydropyridine-3-carboxamide, hydrochloride salt (Compound 2) due to an improved pharmacokinetic profile and reduced inhibition against certain CYP 450 isozymes.

Cytochrome P450 Assay

The ability of compound to inhibit the major human cytochrome P450s (CYPs) responsible for drug metabolism was evaluated in vitro using recombinant human CYP isoforms. The inhibition of cDNA-derived CYP enzymes prepared from baculovirus-infected insect cells was measured using either 3-cyano-7-ethoxycoumarin (CYP1A2, CYP2C19), 7-methoxy-4-trifluoromethylcoumarin (CYP2C9) or 3-[2-(N,N-diethyl-N-methylamino)ethyl]-7-methoxy-4-methylcoumarin (CYP2D6) as the substrates. CYP3A4 inhibition was evaluated with two substrates: 7-benzyloxy-4-trifluoromethylcoumarin (BFC) and resorufin benzyl ether (BzRes). A single concentration of each model substrate (at approximately the apparent K$_m$, with the exception of BFC, which was tested below the apparent K$_m$) and multiple concentrations of the test compounds, separated by approximately ½ log units, were tested in duplicate. Metabolism of the model substrates was assayed by the production of 7-hydroxy-3-cyanocoumarin, 3-[2-(N,N-diethylamino)ethyl]-7-hydroxy-4-methylcoumarin, 7-hydroxy-4-trifluoromethylcoumarin or resorufin, and measured via fluorescence detection. Assays were conducted in 96-well microtiter plates in the presence of an NADPH generating system. Positive control samples were included in these studies. The positive control values were within the historical range for all the assays. The IC$_{50}$ values were calculated utilizing XLfit curve-fitting software.

Pharmacokinetic Parameters Obtained in Mice. In a 8 h oral exposure studies, a single-dose of 50 mg/kg of the compounds were delivered as a solution in 70% PEG400/30% water by oral gavage to fasted adult male Balb/C mice (n=2 or 3 per compound). Three serum samples were collected from each mouse at 0.5, 1, 4, 8 h time points following oral dosing. The first two samples were obtained by retro-orbital bleed (~100 μL/20-25 g mouse) and the third sample by cardiac puncture. The blood samples were allowed to clot on ice, centrifuged and then serum harvested. Plasma samples were stored at −20° C. prior to analysis. The plasma samples were analyzed for parent compound via HPLC coupled tandem mass spectrometry (LC/MS/MS).

| Compound | CYP 3A4-BFC IC50 (µM) | CYP 3A4-BZR IC50 (µM) | Pharmacokinetic Parameters $AUC_{0-8\,h}$ |
|---|---|---|---|
| 1 | 19.89 | 12.27 | 236 µM * hr |
| 2 | 0.51 | 6.40 | 33 µM * hr |

We claim:

1. A compound having the following Formula I:

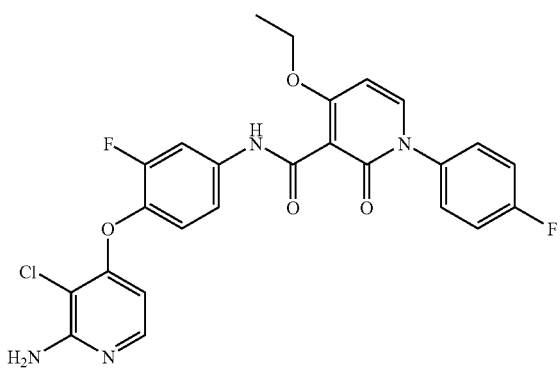

I or a salt thereof.

2. A pharmaceutical composition comprising a therapeutically effective amount of a compound having the following Formula I:

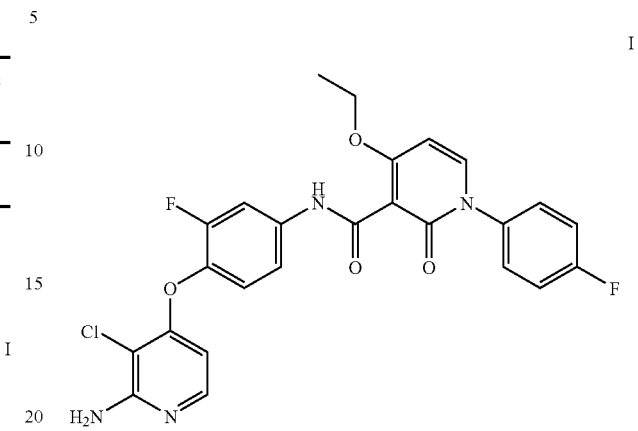

I or a salt thereof in a pharmaceutically acceptable carrier.

3. The pharmaceutical composition according to claim 2 wherein said pharmaceutically acceptable carrier is comprised of microcrystalline cellulose and mannitol or lactose.

4. The pharmaceutical composition according to claim 3 further comprising a lubricating agent.

5. The pharmaceutical composition according to claim 2 further comprising a disintegrating agent.

* * * * *